(12) United States Patent
Tonoike et al.

(10) Patent No.: US 6,472,187 B1
(45) Date of Patent: *Oct. 29, 2002

(54) METHOD FOR AMPLIFICATION OF RNA

(75) Inventors: Hiroshi Tonoike; Naoyuki Nishimura, both of Tsukuba (JP)

(73) Assignee: Shimadzu Corporation, Kyoto (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/610,901

(22) Filed: Jul. 6, 2000

(30) Foreign Application Priority Data

Jul. 16, 1999 (JP) .......................................... 11-202626

(51) Int. Cl.⁷ ........................... C12P 19/34; C12Q 1/68; C07H 21/02; C07H 21/04; C07H 5/04
(52) U.S. Cl. ....................... 435/91.51; 435/6; 435/91.1; 435/91.2; 435/91.21; 435/101; 435/103; 435/183; 536/23.1; 536/24.33; 536/55.1
(58) Field of Search .......................... 435/91.51, 6, 91.2

(56) References Cited

FOREIGN PATENT DOCUMENTS

WO    WO 92/08800    *   5/1992

OTHER PUBLICATIONS

Lee et al. (Focus (1997) 19(2): 39–42).*

Baba et al. "Mechanism of inhibitory effect of dextran sulfate and heparin on replication of human immunodeficiency virus and vivo" (1988) Proc. Natl. Acad. Sci. USA 85:6132–6136.*

* cited by examiner

Primary Examiner—Carla J. Myers
Assistant Examiner—Alexander H. Spiegler
(74) Attorney, Agent, or Firm—Rader, Fishman & Grauer PLLC

(57) ABSTRACT

An object of the present invention is to establish a method for amplifying an RNA in a biologically-derived sample by preparing a reaction solution in which a nucleic acid synthesis is not inhibited even in the presence of various biologically-derived impurities and as well as to enable a convenient, rapid and highly sensitive analysis of the RNA in the sample. In a method of the present invention, a reaction solution having a pH higher than that of an ordinarily employed reaction solution and/or containing a polyamine and/or a sulfated polysaccharide.

17 Claims, 1 Drawing Sheet

```
                       SEQUENCE LISTING

<160> NUMBER OF SEQ ID NOS:    2

<210> SEQ ID NO 1
   <211> LENGTH: 21
   <212> TYPE: DNA
   <213> ORGANISM: Artificial Sequence
   <220> FEATURE:
   <223> OTHER INFORMATION: Description of Artificial Sequence: synthetic
         oligonucleotide

<400> SEQUENCE: 1
caagagatgg ccacggctgc t                                          21

<210> SEQ ID NO 2
   <211> LENGTH: 21
   <212> TYPE: DNA
   <213> ORGANISM: Artificial Sequence
   <220> FEATURE:
   <223> OTHER INFORMATION: Description of Artificial Sequence: synthetic
         oligonucleotide

<400> SEQUENCE: 2
tcgttctgca tcctgtcggc a                                          21
```

METHOD FOR AMPLIFICATION OF RNA

BACKGROUND OF THE INVENTION

1. Field of the Invention

The present invention relates to a method for amplification of RNA, especially to a method for synthesis of RNA by means of a reverse transcriptase-polymerase chain reaction (hereinafter abbreviated as RT-PCR).

Regarding expression of substances in the present specification, the singular form of a substance includes both singular and plural.

2. Description of the Related Art

An RT-PCR method is a procedure in which an RNA is converted into a complementary DNA (cDNA) using a reverse transcriptase and then the cDNA is amplified by a PCR method. Since an RT-PCR method enables a quantitative analysis even with a trace amount of the RNA, it is regarded currently as an analytical method having the highest sensitivity which is essential for a detection of an virus having an RNA as a gene, for a quantitative detection of an mRNA, for an analysis of an expressed gene by a base sequencing, and for an analysis and a production of an expression product by a cDNA cloning.

A PCR method which is conducted subsequently to an RT reaction in an RT-PCR method is a procedure capable of amplifying an intended DNA fragment by several hundred thousand times by repeating a DNA synthesis reaction between the primers sandwiching a certain region of a DNA chain. A PCR method is disclosed in Japanese Laid-open Patent Publication No. S61-274697 which is an invention by Mullis et al.

Another method for amplifying an RNA is an NASBA (Nucleic Acid Sequence Based Amplification) method etc. has been developed. Since this method allows an amplification reaction to be performed directly from an RNA, it is suitable in a study employing an RNA as a template, and thus being brought into use recently.

Furthermore, since an NASBA method involves no denaturation process such as a PCR, it needs no thermal cycles and thus can effect an amplification characteristically at a constant temperature.

However, since any of the RNA amplification methods including those described above is based on an enzymatic reaction, it is well known to allow the reaction to be inhibited potently by pigments, proteins, saccharides or unknown impurities contained in a biological sample.

Accordingly, a process, prior to an RNA amplification described above, for separating a cell, a fungus, a bacterium and a virus etc. (hereinafter referred to as an RNA inclusion body) from a sample followed by extracting an RNA from such RNA inclusion body is required prior to the nucleic acid synthesis described above. Such process has conventionally been a procedure in which a biological sample is treated with an enzyme, a surfactant or a chaotropic agent, etc. and then an RNA is extracted with phenol or phenol/chloroform, etc. Recently, an ion exchange resin, a glass filter, a glass bead or a reagent having a protein coagulating effect is employed in a process for extracting an RNA.

Nevertheless, since any of the methods described above poses a difficulty in removing the impurities completely when employed for purifying an RNA in a sample and frequently fails to recover a nucleic acid in a sample at a constant yield, it fails to allow a subsequent RNA amplification to take place successfully especially when the content of intended nucleic acids in a sample is low. Furthermore, any of these purification methods involves a complicated, time-consuming operation as well as a higher possibility of a contamination during the operation.

Also since an RNA is always at a risk of a degradation by an RNA degrading enzyme (RNase) which is present generally in all biological samples, and it is required to inactivate the RNase rapidly upon a purification and to keep strict operation and control also during and after the purification to ensure no contamination with an RNase.

SUMMARY OF THE INVENTION

An object of the present invention is to provide a novel reaction solution capable of amplifying an RNA in a biological sample efficiently while suppressing a substance having an inhibitory effect on a nucleic acid synthesis, whereby providing a method for amplifying said RNA in said sample by adding said sample or an RNA inclusion body in said sample directly to said reaction solution.

Thus, the present invention is a method for amplification of RNA comprising adding a sample directly to a reaction solution to conduct an RNA amplification reaction whereby amplifying the RNA present in the sample immediately. In this method, a sample may be added to a reaction solution, or, alternatively the reaction solution is added to the sample, thus no order of the addition being specified.

While an RT-PCR method are included in an RNA amplification method in the present invention, they are not limitative and any other methods utilizing enzymatic reactions to amplify an RNA may also be employed.

In the present invention, the expression "adding directly" means that "after a cell, a fungus, a bacterium and a virus etc. (hereinafter referred to as an RNA inclusion body) are separated from a sample prior to an RNA amplificaiton, there is no need of a process for extracting an RNA from such RNA inclusion body".

In the present invention, a sample means an RNA inclusion body in a biological sample or a biological sample itself. A biological sample means an animal or plant tissue, a body fluid, an excreted matter and the like, and an RNA inclusion body means a cell, a fungus, a virus and the like. A body fluid includes a blood-derived sample such as blood, plasma and serum as well as spinal fluid, saliva and milk and the like. An excretion includes urine, feces and the like. A cell may be, but not limited to, a leukocyte separated from a blood or a spinal fluid, as well as an buccal mucosal cell and the like.

The present invention is a method for amplification of RNA described above wherein the pH of said reaction solution for a gene amplification at 25° C. is 8.2 or higher, that at 55° C. is 7.4 or higher, and/or that at 70° C. is 7.1 or higher.

The present invention is a method for amplification of RNA described above wherein a polyamine is added to said reaction system.

The present invention is a method for amplification of RNA described above wherein a sulfated polysaccharide and/or salts thereof (hereinafter referred to together as a sulfated polysaccharide) is added to said reaction system.

The present invention is a method for amplification of RNA described above wherein the pH of said reaction solution for a gene amplification at 25° C. is 8.2 or higher, that at 55° C. is 7.4 or higher, and/or that at 70° C. is 7.1 or higher; and/or at least one of a polyamine, a sulfated polysaccharide and/or salts thereof and dithiothreitol are added to said reaction system.

The present invention allows a biologically-derived sample to be added directly to a reaction solution to effect a direct amplification of an RNA which is present in the sample. Thus, the invention enables a convenient, rapid and highly sensitive detection of a foreign organism such as an RNA virus including hepatitis C virus (HCV) existing latently in a biologically-derived sample, and a retrovirus including a human immunodeficiency virus (HIV) as well as a variant cell such as a carcinoma cell existing as a cell which is now quite distinct from a host cell. The invention also allows a detection of an mRNA which is subjected to an intracellular transcription, an analysis of an expression gene by a base sequencing and an analysis and a production of an expression product by a cDNA cloning to be performed conveniently and rapidly. Furthermore, the invention which employs a direct amplification of an RNA from a biologically-derived sample can avoid the effect of an RNA degradation by an RNase which has conventionally been experienced during an extraction and a purification of an RNA.

DETAILED DESCRIPTION OF THE INVENTION

Figure 1:
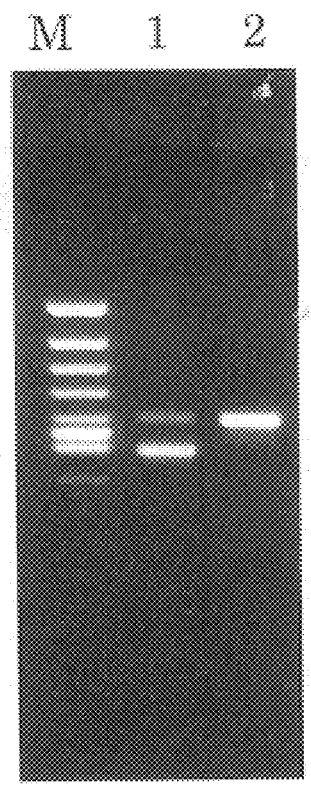
FIG. 1 shows the results of a gel electrophoresis performed for detecting an RNA amplified in Experimental Example 1.

The present invention is a method for amplification of RNA comprising adding an RNA inclusion body in a biological sample or a sample itself directly to a reaction solution to effect an RNA amplificaiton reaction, whereby amplifying said RNA immediately.

In the present invention, for the purpose of embodying a method for amplifying an RNA described above, the pH of a reaction solution to which the sample is added is 8.2 or higher, preferably 8.8 to 9.2, at 25° C., 7.4 or higher, preferably 8.0 to 8.4, at 55° C., and/or 7.1 or higher, preferably 7.7 to 8.1, at 70° C.

The pH of a reaction solution, when the sample is a blood-derived sample such as blood, plasma and serum, is preferably approximately 8.9 at 25° C., approximately 8.1 at 55° C. and/or approximately 7.8 at 70° C.

Also in the present invention, for the purpose of embodying a method for amplifying an RNA described above, a polyamine is added to a reaction solution in a nucleic acid synthesis method for amplifying an intended RNA in a sample. Such polyamine may be added first to a sample and then to a reaction solution, or, polyamine may alternatively be added directly to a reaction solution. Even when a polyamine is not contained uniformly in a reaction solution (for example when a polyamine is added to a sample and the sample is added to a reaction solution without stirring), it exhibits a similar effect. Only a single polyamine may be employed, or a combination of several polyamines may be employed.

Such polyamine is a generic name of a hydrocarbon having two or more primary or secondary amino groups. While some of the polyamines exist in vivo and are contained in large amounts in a tissue undergoing extensive synthesis of proteins and nucleic acids, thus exerting various physiological effects, such effects are not necessarily possessed by a polyamine employed in the present invention, and any polyamine which is a hydrocarbon having two or more primary or secondary amino groups in its molecule may be employed without any limitation.

Those exemplified typically are a straight polyamine having in its molecule two amino groups (ethylenediamine, trimethylenediamine, putrescine), a straight polyamine having 3 amino groups (spermidine, diethylenetriamine), a straight polyamine having four amino groups (spermine, triethylenetetramine), a straight polyamine having five amino groups (tetraethylenepentamine), a straight polyamine having 6 amino groups (pentaethylenehexamine), a cyclic polyamine (1,4-bis(3-aminopropyl)-piperazine, 1-(2-aminoethyl)piperazine, 1-(2-aminoethyl)piperidine, 1,4,10,13-tetraoxa-7,16-diazacyclooctadecane and tris(2-aminoethyl)amine and the like.

The amount (concentration) of a polyamine to be added may vary depending on the type of the polyamine, the type or concentration of the sample and the like, the effect can be exerted at a higher concentration when the number of the amino groups in the molecule is smaller and at a lower concentration when the number of the amino groups is larger. For example, ethylenediamine having 2 amino groups is added preferably at a concentration of about 8 mM, while tetraethylenepentamine and pentaethylene hexamine which have 5 or more amino groups exert inhibitory effects on the amplification reaction when added at 4 mM or higher and thus are added preferably at concentrations not higher than 2 mM.

Also in the present invention, for the purpose of embodying a method for amplifying an RNA described above, a sulfated polysaccharide is added to a reaction solution in a nucleic acid synthesis method for amplifying an intended RNA in a sample. Such sulfated polysaccharide may be added first to a sample and then to a reaction solution, or, sulfated polysaccharide may alternatively be added directly to a reaction solution. Even when a sulfated polysaccharide is not contained uniformly in a reaction solution (for example when a sulfated polysaccharide is added to a sample and the sample is added to a reaction solution without stirring), it exhibits a similar effect. Only a single sulfated polysaccharide may be employed, or a combination of several sulfated polysaccharides may be employed.

While heparin and salts thereof and dextran sulfate and salts thereof are the sulfated polysaccharides employed preferably in the present invention, they are not limitative and other substances such as heparan sulfate, chondroitin sulfate, dermatan sulfate, Funoran, sulfated agarose, carragheenan, Porphyran, Fucoidan, sulfated Curdlan may be employed.

The amount (concentration) of a sulfated polysaccharide to be added may vary depending on the type of the sulfated polysaccharide, the type or concentration of the sample and the like, it is preferably 0.4 to 25 µg/ml in a reaction solution when using a sample derived from a blood and heparin as a sulfated polysaccharide. When using a sample derived from a blood and dextran sulfate as a sulfated polysaccharide, the concentration is preferably 0.05 to 8 µg/ml in a reaction solution.

An RT reaction solution generally contains a pH buffer solution, salts such as $MgCl_2$ and KCl, dithiothreitol (DTT), a primer or primers, deoxyribonucleotides, an RNase inhibitor and a reverse transcriptase. The salts exemplified above may appropriately be changed to other salts. Those which may sometimes be added are proteins such as gelatin and albumin as well as a surfactants and the like.

A reaction solution of a PCR conducted subsequently to an RT reaction in an RT-PCR generally contains a pH buffer solution, salts such as MgCl$_2$ and KCl, primers, deoxyribonucleotides and a heat-resistant polymerase. The salts exemplified above may appropriately be changed to other salts. Those which may sometimes be added are proteins such as gelatin and albumin as well as dimethylsulfoxide, a surfactants and the like.

An RT-PCR may be performed by adding a part of an RT reaction product to a PCR reaction solution (two tube-two step), or may be performed by adding a PCR reaction reagent to an RT reaction product (one tube-two step), or may be performed as a continuos process of an RT reaction followed by a PCR with providing all reagents required for an RT-PCT reaction in advance (one tube-one step).

A pH buffer solution is a combination of tris (hydroxymethyl)aminomethane and a mineral acid such as hydrochloric acid, nitric acid and sulfuric acid, with hydrochloric acid being preferred as a mineral acid. Various other pH buffer solutions such as a combination of tricine, CAPSO (3-N-cyclohexylamino-2-hydroxypropanesulfonic acid) or CHES (2-(cyclohexylamino)ethanesulfonic acid) with sodium hydroxide or potassium hydroxide may also be employed. A buffer solution whose pH is adjusted is used frequently at a concentration of 10 mM to 100 mM in a gene amplification reaction solution.

A primer means an oligonucleotide which serves as a synthesis initiation point for a cDNA synthesis or a nucleic acid amplification. While a single-stranded primer is preferable, a double-stranded primer may also be employed. When a double-stranded primer is employed, the primer is preferably converted into a single-stranded primer prior to a reaction. A primer may be synthesized by a known method, or may be isolated from a naturally-occurring wild type.

A reverse transcriptase employed in an RT reaction means an enzyme capable of transcribing an RNA reversely into a cDNA. Non-limiting examples of such reverse transcriptase are a reverse transcriptase derived from an avian retrovirus such as Rous associated virus (RAV) and Avian myeloblastosis virus (AMV), a reverse transcriptase derived from a murine retrovirus (MMLV) such as Moloney murine leukemia virus (MMLV) or Tth DNA polymerase described above.

An RT reaction of the present invention preferably employs a reverse transcriptase derived from an avian retrovirus, especially derived from AMV.

A heat-resistant polymerase employed in a PCR means a polymerase having an excellent heat resistance which synthesizes a nucleic acid in response to a primer addition. Non-limiting examples of an appropriate heat-resistant polymerase are Thermus aquaticus-derived Taq DNA polymerase, Thermus thermophilus-derived Tth DNA polymerase, Pyrococcus-derived KOD, Pfu or Pwo DNA polymerase, or a mixture of these heat-resistant polymerases. Tth DNA polymerase can conveniently be employed as a sole enzyme to perform an RT-PCR in the one tube-one step process, since Tth DNA polymerase also has an RT activity.

A procedure for synthesis of nucleic acids according to the present invention is similar to an ordinary procedure except for the use of a reaction solution whose pH is higher than that employed usually and/or the addition of a polyamine and/or a sulfated polysaccharide. Thus, in an RT reaction, the reaction is proceeded for about 30 minutes to 1 hour at a temperature suitable for a primer and a reverse transcriptase selected. In a PCR, a DNA is first converted into a single-stranded DNA by means of a thermal denaturation (denaturation step). Secondly, the primers between which a region to be amplified is sandwiched are hybridized (annealing step). Subsequently, the primers are elongated by a DNA polymerase in the presence of 4 deoxyribonucleotides (dATP, dGTP, dCTP, dTTP) (polymerization step).

EXAMPLES

The present invention is further described in the following examples which are not intended to restrict the invention.

Experimental Example 1

In this experiment, a human blood was added directly to a reaction solution established in the present invention to perform an RT-PCR using a primer specific to a human beta-actin mRNA. In the RT-PCR, 1 µl of the human blood was added to 50 µl of the reaction solution.

The primer for the RT reaction was an oligonucleotide (BAR) having the sequence complementary to the human beta-actin mRNA, and then in the subsequent PCR an oligonucleotide (BAF) having the base sequence complementary to the cDNA synthesized in the RT reaction was employed additionally. In order to distinguish an RNA-derived product from a DNA-derived product in the RT-PCR, the BAF primer was set to a human beta-actin gene exon 3 and the BAR primer to the exon 4, whereby designing an intron of 107 bp being sandwiched between the both primers. Accordingly in the RT-PCR in this experiment the RNA-derived product consisted of 264 bp and the DNA-derived product consisted of 370 bp. The sequences of the primers employed are as follows.

BAF: 5' CAAGAGATGGCCACGGCTGCT 3' (Seq. ID. No. 1)

BAR: 5' TCGTTCTGCATCCTGTCGGCA 3' (Seq. ID. No. 2)

The RT reaction solution used was a solution (pH8.9) containing 10 mM Tris-HCl, 35 mM KCl, 1.5 mM MgCl$_2$, 200 µM each of DATP, dCTP, dGTP and dTTP, 2 mM DTT, 0.4 µM of the BAR primer, 50 units/50 µl Ribonuclease Inhibitor (Takara shuzo, Kyoto, Japan), and 5 units/50 µl AMV XL reverse transcriptase (Takara shuzo), together with a polyamine and a sulfated polysaccharide. In this experiment, triethylenetetramin was added as a polyamine at the concentration of 2 mM. As a sulfated polysaccharide, heparin Na was added at the concentration of 0.8 µg/ml.

In the PCR subsequent to the RT reaction, 20 pmol of the BAF primer and 1.25 units of Taq DNA polymerase (TaKaRa Taq: Takara shuzo) were added to the RT reaction solution described above.

The RT reaction was performed at 55° C. for 30 minutes, followed by a treatment at 95° C. for 5 minutes, whereby inactivating the reverse transcritase.

After this procedure, the BAF primer and the Taq DNA polymerase were added to perform a PCR. The PCR involved 50 cycles, each cycle consisting of 30 seconds at 94° C. followed by 30 seconds at 68° C. followed by 60 seconds at 72° C., and then the final polymerization at 72° C. for 7 minutes. After completing the PCR, 5 µl of the reaction solution was subjected to an electrophoresis on 2.5% agarose gel in TAE (40 mM Tris-acetate, 1 mM EDTA) containing 0.5 µg/ml ethidium bromide to detect the amplification product.

FIG. 1 shows the results of the electrophoresis of an amplification product obtained by an RT-PCR in which 1 µl of the human blood was added directly to 50 µl of the reaction solution.

In this figure, "M" represents a size marker (250 ng of φ X174-RF DNA obtained by a cleavage with HincII), "1" shows the results of the RT-PCR in the presence of the reverse transcriptase and "2" shows the results in the absence of the reverse transcriptase for reference.

Based on the results described above, an amplification product specific to the human beta-actin mRNA (arrow) was obtained in the RT-PCR performed in the presence of the reverse transcriptase by adding a human blood directly to the reaction solution (Lane 1). The amplification products shown above the arrow are the DNA amplification products which were amplified by the PCR.

Experimental Example 2

In this experiment, a human blood was treated with a hypotonic solution to effect a hemolysis and then centrifuged to remove the supernatant to obtain a leukocyte pellet, to which the reaction solution was added similar to that in Experimental Example 1, whereby effecting an RT-PCR. The RT-PCR and the detection of the RNA amplification products by an electrophoresis were conducted in the conditions similar to those in Experimental Example 1.

Figure 2:
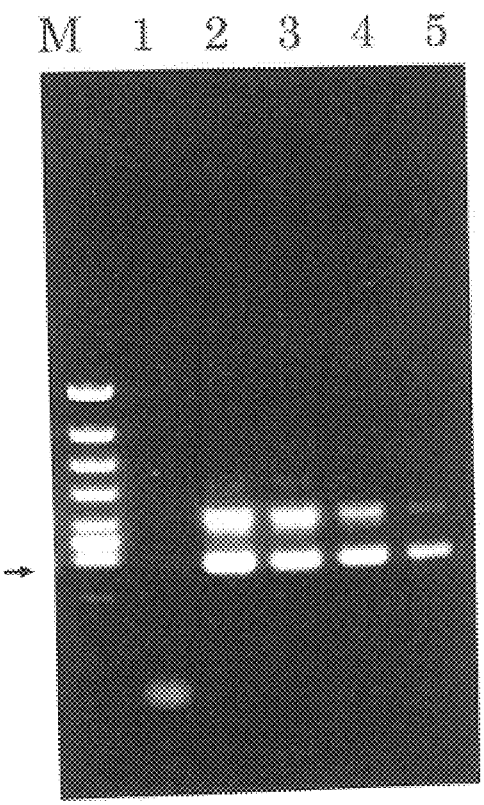
FIG. 2 shows the results of a gel electrophoresis performed for detecting an RNA amplified in Experimental Example 2.

To various amounts of the leukocyte pellet, 50 µl of the reaction solution were added to perform the RT-PCR and the results of the electrophoresis of the amplification products are shown in FIG. 2.

In this figure, "M" represents a size marker (250 ng of φ X174-RF DNA obtained by a cleavage with HincII), "2", "3", "4" and "5" show the results of the RT-PCR in which the leukocyte pellet prepared by treating 10 µl, 20 µl, 40 µl and 80 µl of a human blood, respectively, of the blood were combined with 50 µl of the reaction solution. "1" shows the results of a control RT-PCR in the absence of the leukocyte.

Based on the results described above, an amplification product specific to the human beta-actin mRNA (arrow) was obtained at any level of the leukocyte added in the RT-PCR in which a reaction solution of the present invention was added to the human leukocyte pellet. The amplification products shown above the arrow are the DNA amplification products which were amplified by the PCR.

FIG. 2 also demonstrates that an amplification product specific to the human beta-actin mRNA was obtained even when the leukocyte obtained by treating the blood in an amount as large as 80 µl was subjected to the RT-PCR (Lane 5).

The results described above revealed that an RT-PCR employing a reaction solution of the present invention enables an RNA analysis of a large amount of leukocyte. Accordingly, an RNA expressed in a part of cells, or an RNA expressed in a trace amount in a cell can directly be analyzed from a sample or an RNA inclusion body in a sample by employing a method according to the present invention.

What is claimed is:

1. A one tube-two step polymerase chain reaction method for amplification of a target RNA in a biological sample comprising the steps of:
   a) providing in the tube a reaction solution for reverse transcription comprising a reverse transcriptase and at least one of a polyamine, a sulfated polysaccharide, a salt thereof, or a mixture thereof;
   b) incubating the biological sample under conditions that produce a reverse transcription product; and
   c) incubating the reverse transcription product with a subsequently added DNA synthesizing enzyme under conditions that produce a polymerase chain reaction product.

2. The method for amplification of RNA according to claim 1, wherein in step a.) the pH of said reaction solution at 25° C. is 8.2 or higher, or at 55° C. is 7.4 or higher, or at 70° C. is 7.1 or higher.

3. The method for amplification of RNA according to claim 1, wherein a polyamine is added to said reaction solution.

4. The method for amplification of RNA according to claim 3, wherein said polyamine is selected from the group consisting of ethylenediamine, trimethylenediamine, putrescine, spermidine, spermine, diethylenetriamine, triethylenetetramine, tetraethylenepentamine, pentaethylenehexamine, 1,4-bis(3-aminopropyl)-piperazine, 1-(2-aminoethyl)piperazine, 1-(2-aminoethyl)piperidine, 1,4,10,13-tetraoxa-7,16-diazacyclooctadecane and tris(2-aminoethyl)amine.

5. The method for amplification of RNA according to claim 1, wherein a sulfated polysaccharide, a salt thereof, or a mixture thereof, is added to said reaction solution.

6. The method for amplification of RNA according to claim 5, wherein said sulfated polysaccharide is selected from the group consisting of heparin, a salt thereof, dextran sulfate, a salt thereof, and a mixture thereof.

7. The method for amplification of RNA according to claim 6, wherein heparin, a salt thereof, or a combination thereof, is added at a concentration of 0.4 to 25 µg/ml to said reaction solution.

8. The method for amplification of RNA according to claim 6, wherein dextran sulfate, a salt thereof, or a mixture thereof, is added at a concentration of 0.05 to 8 µg/ml to said reaction solution.

9. The method for amplification of RNA according to claim 1, wherein in step a.) the pH of said reaction solution at 25° C. is 8.2 or higher, or at 55° C. is 7.4 or higher, or at 70° C. is 7.1 or higher, and at least one of a polyamine, a sulfated polysaccharide, a salt thereof, or a mixture thereof, is added to said reaction solution.

10. The method for amplification of RNA according to claim 1, wherein said biological sample contains an RNA inclusion body.

11. A one tube-one step method for amplification of a target RNA in a biological sample comprising the steps of:

a) providing in the tube a reaction solution for a reverse transcription and a polymerase chain reaction comprising a reverse transcriptase, a DNA synthesizing enzyme and at least one of a polyamine, a sulfated polysaccharide, a salt thereof, or a mixture thereof;

b) incubating the biological sample under conditions that produce a reverse transcription product; and c) incubating the reverse transcription product with the DNA synthesizing enzyme under conditions that produce a polymerase chain reaction product.

12. The method for amplification of a target RNA according to claim 11, wherein in step a.) the pH of the reaction solution at 25° C. is 8.2 or higher, or at 55° C. is 7.4 or higher, or at 70° C. is 7.1 or higher.

13. The method for amplification of RNA according to claim 11, wherein said polyamine is selected from the group consisting of ethylenediamine, trimethylenediamine, putrescine, spermidine, spermine, diethylenetriamine, triethylenetetramine, tetraethylenepentamine, pentaethylenehexamine, 1,4-bis(3-aminopropyl)-piperazine, 1-(2-aminoethyl)piperazine, 1-(2-aminoethyl)piperidine, 1,4,10,13-tetraoxa-7,16-diazacyclooctadecane and tris(2-aminoethyl)amine.

14. The method for amplification of a target RNA according to claim 11, wherein the sulfated polysaccharide is selected from the group consisting of heparin, a salt thereof, dextran sulfate, a salt thereof, and a mixture thereof.

15. The method for amplification of a target RNA according to claim 14, wherein heparin, a salt thereof, or a combination thereof, is added at a concentration of 0.4 to 25 µg/ml to the reaction solution in step a) of claim 11.

16. The method for amplification of a target RNA according to claim 14, wherein dextran sulfate, a salt thereof, or a mixture thereof, is added at a concentration of 0.05 to 8 µg/ml to the reaction solution in step a) of claim 11.

17. The method for amplification of a target RNA according to claim 11, wherein the biological sample contains an RNA inclusion body.

* * * * *